(12) United States Patent
Aime et al.

(10) Patent No.: US 8,211,404 B2
(45) Date of Patent: Jul. 3, 2012

(54) IONIC AND NON-IONIC RADIOGRAHIC CONTRAST AGENTS FOR USE IN COMBINED X-RAY AND NUCLEAR MAGNETIC RESONANCE DIAGNOSTICS

(75) Inventors: Silvio Aime, Milan (IT); Alessandro Barge, Milan (IT); Valentina Mainero, Milan (IT)

(73) Assignee: Bracco Imaging S.p.A., Milan (IT)

( * ) Notice: Subject to any disclaimer, the term of this patent is extended or adjusted under 35 U.S.C. 154(b) by 0 days.

(21) Appl. No.: 10/485,878

(22) PCT Filed: Jul. 23, 2002

(86) PCT No.: PCT/EP02/08183
§ 371 (c)(1),
(2), (4) Date: Dec. 6, 2004

(87) PCT Pub. No.: WO03/013616
PCT Pub. Date: Feb. 20, 2003

(65) Prior Publication Data
US 2005/0113675 A1 May 26, 2005

(30) Foreign Application Priority Data
Aug. 3, 2001 (IT) .............................. MI2001A1706

(51) Int. Cl.
*A61B 5/055* (2006.01)
*A61K 49/00* (2006.01)
(52) U.S. Cl. .......................................... 424/9.1; 424/9.3
(58) Field of Classification Search .................... 424/9.3
See application file for complete search history.

(56) References Cited

U.S. PATENT DOCUMENTS

2005/0136002 A1  6/2005  Fossheim et al.

FOREIGN PATENT DOCUMENTS

| EP | 0118348 | * | 2/1984 |
| EP | 0 759 785 | | 3/1997 |
| WO | WO0066180 | * | 11/2000 |
| WO | WO00/75141 | | 12/2000 |

OTHER PUBLICATIONS

Henkelman et al. (NMR Biomed. 2001, 14, 57-64).*
Parker et al. (Invest. Radiol. 1998, 33, 560-572).*
Mathews et al. (AJR 1995, 164, 169-172).*
Wolff et al. (Radiology 1994, 192, 593-599).*
Alberico et al. (AJNR Am. J. Neuroradiol. 1999, 20, 328-334).*
Mehta et al. (Radiol. 1995, 195, 41-46; abstract).*
Mathews et al. (JMRI, 1997, 7, 14-22).*
PCT International Search Report for PCT/EP02/08183 dated Jan. 31, 2003.
PCT International Preliminary Examination Report for PCT/EP02/08183 dated Jan. 15, 2004.
Hergan et al.; "Effects of iodinated contrast agents in MR imaging", European Journal of Radiology, vol. 21, 1995, pp. 11-17.
Ward et al; "A new class of contrast agents for MRI based on proton chemical exchange dependent saturation transfer (CEST)", Journal of Magnetic Resonance, vol. 143, 2000, pp. 79-87.
Aime et al., "Iopamidol: Exploring the Potential Use of a Well-Established X-Ray Contrast Agent for MRI," Mag. Res. Med., vol. 53, pp. 830-834 (2005).
Ward et al., "Determination of pH Using Water Protons and Chemical Exchange Dependent Saturation Transfer (CEST)," Mag. Res. Med., vol. 44, pp. 799-802 (2000).
Sun et al., "Correction for Artifacts Induced by $B_0$ and $B_1$ Field Inhomogeneities in pH-Sensitive Chemical Exchange Saturation Transfer (CEST) Imaging," Mag. Res. Med., vol. 58, pp. 1207-1215 (2007).
Mittal et al., "A Prospective Comparison of Brain Contrast Characteristics and Lesion Detection Using Single-Shot Fast Spin-Echo and Fast Spin-Echo," Neuroradiology, vol. 41, pp. 480-486 (1999).
McKenzie et al., "Three-Dimensional Delayed Gadolinium-Enhanced MRI of Cartilage (dGEMRIC) at 1.5T and 3.0T," J. Mag. Res. Imaging, vol. 24, pp. 928-933 (2006).
Office Action issued for U.S. Appl. No. 12/635,161, mailed on Mar. 9, 2012.

* cited by examiner

Primary Examiner — Michael G Hartley
Assistant Examiner — Melissa Perreira
(74) Attorney, Agent, or Firm — Pearl Cohen Zedek Latzer, LLP

(57) ABSTRACT

The invention discloses the use of ionic and non-ionic radiographic contrast agents for combined X-ray and nuclear magnetic resonance (MRI) diagnostics.

Figure 1:
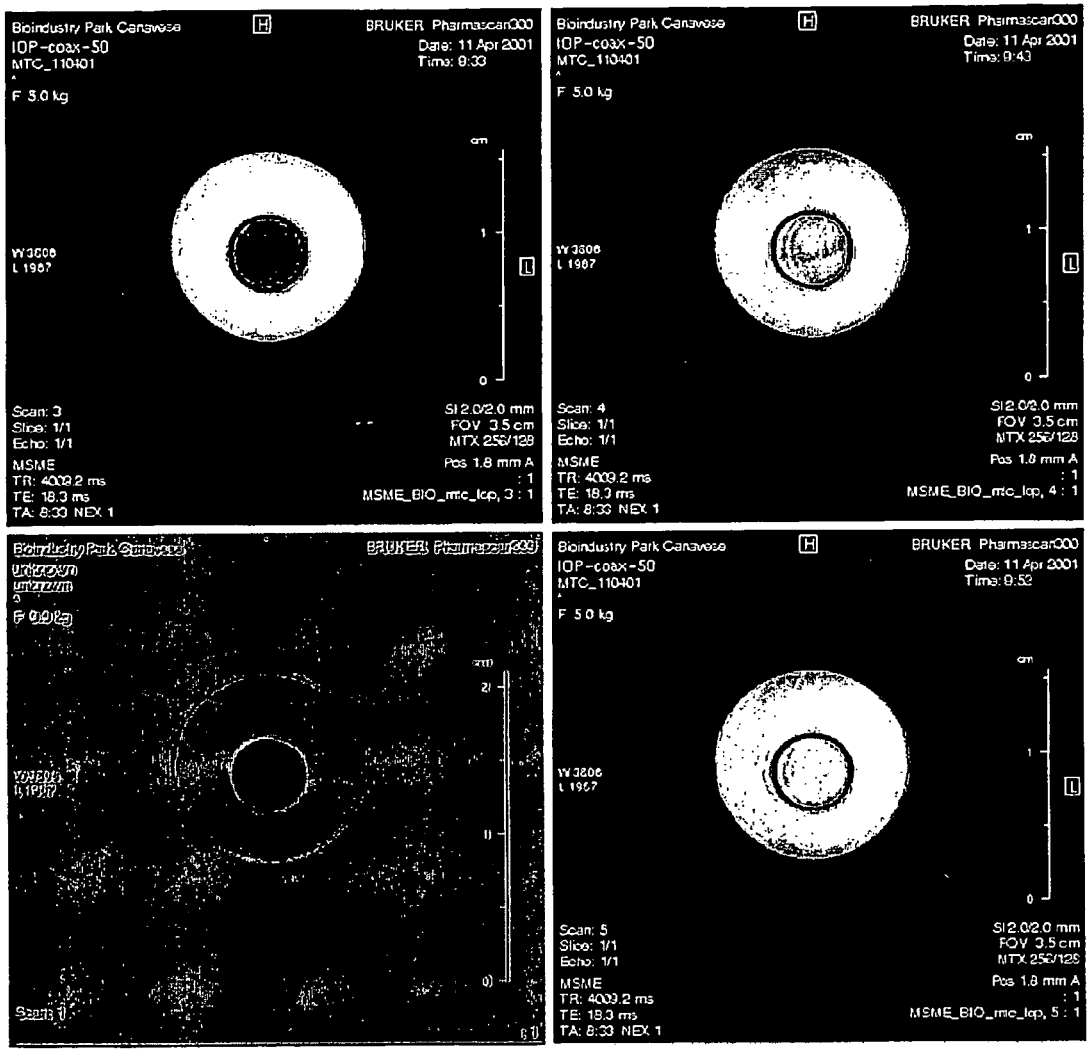

18 Claims, 3 Drawing Sheets

IONIC AND NON-IONIC RADIOGRAHIC CONTRAST AGENTS FOR USE IN COMBINED X-RAY AND NUCLEAR MAGNETIC RESONANCE DIAGNOSTICS

This application is the national stage filing of corresponding international application number PCT/EP02/08183, filed Jul. 23, 2002, which claims priority of Italian Application No. MI2001A001706, filed Aug. 3, 2001, all of which are hereby incorporated by reference.

The present invention discloses the use of radiographic contrast agents for the preparation of diagnostic formulations for the sequential or simultaneous X ray and nuclear magnetic resonance (MRI) diagnostics.

X-ray contrast agents used in in vivo diagnostics are usually characterized by high water solubility, low viscosity, low osmotic pressure, high contrast density, low toxicity and good tolerability.

The clinical use of non-ionic contrast agents has gradually replaced that of ionic contrast agents which, on the other hand, are still being used (see e.g. Renografin) in some diagnostic applications.

Examples of non-ionic contrastographic agents comprise Ioexol, Iomeprol, Iopentol, Iopromide, Ioversol, Ioxilan, Iodixanol and Iopamidol.

Magnetic Resonance Imaging diagnostic procedures mainly use paramagnetic compounds, preferably chelated complexes of bi- or trivalent paramagnetic metal ions with polyaminopolycarboxylic acids and/or their derivatives or analogues.

Currently available MRI contrast agents comprise: Gd-DTPA, MAGNEVIST®; Gd-DOTA, DOTAREM®; Gd-HPDO3A PROHANCE®; Gd-DTPA-BMA, OMNISCAN®.

The contrast agents listed above are designed for a wholly general use. In fact, after intravenous administration, the MRI contrast agent is distributed in the extracellular spaces in different parts of the body prior to being excreted. In this sense they are similar to iodine compounds used in X ray medical diagnosis.

A recently proposed technique for MRI diagnostic is the magnetization transfer technique (see e.g. J. Chem. Phys. 39 (11), 2892-2901, 1963), in which the proton signal of a molecule, present in the medium or added thereto, is suitably irradiated with a radiofrequency signal generated by the apparatus magnetic field, and transferred through magnetization to the water molecules surrounding the compound, i.e. the so-called "bulk water" of the medium.

The parameters affecting this process are related to different factors such as the nature of the chemical group involved in the proton transfer, the pH of the solution, the temperature of the medium and the intensity of the applied magnetic field.

U.S. Pat. No. 5,050,609 discloses the use of the saturation transfer technique in magnetic resonance, which consists in the magnetization transfer in the presence of an irradiating field able to saturate the protons involved in the exchange process, which procedure is used in vitro and provides further information from the analyzed samples, e.g. biological tissues, polymeric compounds or samples of solid compounds of geologic interest.

Mag. Res. In Medicine, 44, 799-802, 2000, describes a procedure for the determination of the pH in solution using the magnetization signal transfer technique in MRI, in the presence of 5-hydroxy trypthophan or 5,6-dihydrouracil.

J. Mag. Res., 133, 36-45, 1998 and J. Mag. Resonance Imag., 12, 745-748, 2000 describe in vivo and in vitro MRI imaging procedures involving the determination of the proton exchange between metabolites such as urea and water.

Investigative Radiology, 23, S267-270, 1988, describes the effect of some compounds, such as arginine, glycine, Iopamidol, ornithine, serine and serinol, in MRI, in inducing a contrast increase by decreasing T2 relaxation time, i.e. transversal relaxation time of water protons. The decrease of T2, which is experimentally observed, causes a decrease in the intensity of the resulting imaging signal, and this is mainly ascribed to the chemical exchange between the mobile proton of the molecule and bulk water.

Mag. Res. Med. 35, 30-42, 1996 reports an interesting study on the effect of proton exchange between amino acids and water surrounding the compound in MRI, as a function of pH, temperature and presence of some compounds acting as exchange catalysts in the medium.

Furthermore, both J. of Mag. Res., 143, 79-87, 2000 and WO00/66180 disclose the use of some compounds in MRI with saturation transfer techniques of the proton signal.

The compounds used for this purpose belong to different chemical classes, consisting of sugars (e.g. mannitol, sorbitol, fructose, maltose, lactose and dextran), amino acids (e.g. L-Ala, L-Arg, L-Lys), nucleosides, purine and pyrimidine bases, barbituric acid, imidazole compounds and other heterocyclic compounds.

A large number of compounds have been suggested as contrast agents for imaging of the vascular system and of the extra-vasal space, but the parenteral use thereof can involve unwanted side-effects which make their clinical use in vivo troublesome, although their enteral toxicity is not particularly high (see, for instance, *Merck Index* 12$^{th}$ *ed.*: 972. Barbital LD orally in mice: 600 mg/Kg; 973. Barbituric Acid LD50 orally in male rats: >5000 mg/kg; 4475. Guanidine LD orally in rabbits: 500 mg/kg *RTECS Vol.* 5 and. 1985-86: 82776. Thymidine LD50 intraperitoneal mouse 2512 mg/kg; 60194. Pipecolinic Acid LD50 intravenous mouse 2200 mg/kg; 9721. L-Arginine LD50 intravenous mouse 2030 mg/kg; 41867. 2-Imidazolidinone LD50 intraperitoneal mouse 500 mg/kg; 41826. 2-Imidazolidinetione LD50 intraperitoneal mouse 200 mg/kg).

Nowadays, one of the most pressing requests by the medical class concerns the availability of innovative contrast media for specific organs or disorders, which usually are not effectively evidenced with the known techniques.

X ray diagnostic contrast agents are an extremely versatile and interesting class of compounds widely used in clinics thanks to their effectiveness, low toxicity and safety of use in diagnosis concerning different districts of the human body, such as in urography, angiography, ventriculography and myelography.

The use of the same contrast medium for both X ray radiology and MRI diagnostics would remarkably widen the diagnostic potentialities of the compound used and provide diagnostic results so far unexpected.

The availability of a single contrast agent providing diagnostic results through different techniques, which previously required the use of different contrast agents, is an important innovative aspect of the diagnostic technique, particularly in clinics, where diagnostic procedures based on both the usual radiographic procedures, computerized axial tomography (CAT) and magnetic resonance imaging are nowadays employed.

In case of iodinated contrast agents, the use of a single compound for a number of diagnostic procedures would be advantageous also since the total amount of the administered product is by far higher than that of other medicaments.

By way of example, the dose of opacifying agent being injected can reach and even exceed 150 g and the combination of two diagnostic techniques would be cost-saving.

Therefore, the object of the present invention is the use of a iodinated contrast agent comprising at least one amido function for the preparation of a diagnostic formulation to obtain in vitro or in vivo images using magnetization transfer MRI techniques.

"Iodinated contrast agents comprising at least one amido function" herein means iodinated aromatic compounds having a triiodinated aromatic ring bearing at the remaining positions straight or branched, functionally substituted organic residues or an organic compound comprising at least two triiodinated aromatic residues mutually covalently linked at one of the positions, either directly or through a straight or branched, functionally substituted organic residue, said aromatic ring being further substituted at the remaining positions by straight or branched, functionally substituted organic residues and in which the organic residues and the triiodinated aromatic ring are linked by amido functions.

Examples of contrast agents for use according to the invention comprise the compounds of general formula (I) and (II), (III) and (IV) reported below, the corresponding isomers and stereoisomers, in particular the exo, endo regioisomers; the corresponding enantiomeric, racemic and meso forms as well as the salts thereof with physiologically compatible bases or acids.

The method of the invention is based on the use of iodinated contrast agents having mobile protons able to exchange with bulk water, i.e. the surrounding water molecules present in the medium and in the biological tissues.

Irradiation of the mobile proton(s) of the considered molecule with a radiofrequency field tuned on the resonance frequency of the concerned proton(s) induces saturation transfer to the bulk water signal caused by the chemical exchange between the proton of the "exogen" molecule and water. As a result, the saturation of the water signal appears as a decrease in the signal intensity in the MRI image obtained at the body site and/or on in vivo or in vitro samples, involved in the saturation transfer.

The used procedure consists in the use of the contrast medium in vivo or in vitro and in performing the radiological and/or MRI diagnostic analysis at different times and depending on the used technique, starting from one or the other diagnostic procedure.

The resulting MRI images are suitably acquired before, during and/or after irradiation in the radiofrequency field of the proton that exchanges with the water of the medium. The result from the experimentation allows to compare images obtained with X rays and with MRI.

The sequence of the radiological and MRI techniques, which are considered complementary, can be reversed, depending on the body site concerned and the diagnostic analysis. In fact, it may be convenient to carry out first MRI on the body angiographic district, then a radiological urographic investigation.

A further object of the present invention is the use of the disclosed MRI diagnostic technique alone, using the above defined iodinated compounds as contrast agents.

According to the invention the advantages deriving from the use of this class of compounds are that they have known, low in vivo and in vitro toxicity, which makes them easy to use at different dosages, depending on the product used and on the concerned body site. Other advantageous aspects of these compounds are their high water solubility and chemical stability, and well-established pharmacokinetic (see e.g. RoFo Suppl. 128, 220-223 (1989); Invest. Radio.,18, 368-374, 1983; Invest. Radio., 26, S156-S158, 1991) in terms of transport rate in circulation or in other body cavities, retention time in the organs being under examinated, excretion and clearance.

The effect generated by saturation transfer of the protons of the contrast agent molecule causes a decrease in the resulting MRI water proton signal, which is the most important contribution to Magnetic Resonance images.

A first preferred group of iodinated contrast agents comprising amido functions are the compounds of formula (I)

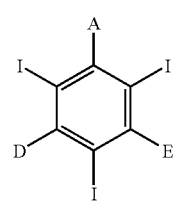

(I)

in which:

A, D, E, which can be the same or different, are groups of formula —CON(R)R$_1$, —COOH, —CONH$_2$ or —N(R)—COR$_2$ or CH$_2$N(R)—COR$_2$;

R is H or R$_1$, with the proviso that the substituent R is H in at least one group of the compound;

R$_1$ is a straight or branched (C$_1$-C$_6$)alkyl residue, optionally substituted with 1-5 hydroxy and/or alkoxy and/or hydroxy-alkoxy groups, or with a NH—CO—R$_1$ or —CO—N(R)R$_1$ group, or R$_1$ is a carbohydrate residue;

R$_2$ is a straight or branched (C$_1$-C$_6$)alkyl residue, optionally substituted with 1-5 hydroxy and/or alkoxy and/or hydroxyalkoxy groups and optionally interrupted by an oxo group.

A second preferred group of iodinated contrast agents comprising amido functions includes compounds of formula (II)

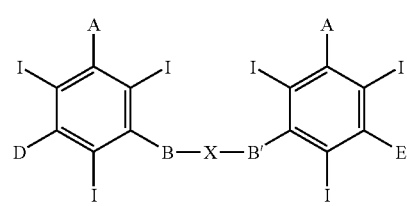

(II)

in which:

A, D and E are as defined above;

B and B', which can be the same or different, are selected from —CO—N(R)—, —N(R)—CO— or —N(COR$_3$)— groups, in which R is H or a residue of a straight or branched (C$_1$-C$_6$)alkyl group, optionally substituted with 1-5 hydroxy and/or alkoxy and/or hydroxyalkoxy groups; R$_3$ is a (C$_1$-C$_3$) alkyl residue, optionally substituted with 1-2 hydroxy or alkoxy or hydroxyalkoxy groups;

X is a covalent bond or a straight or branched (C$_1$-C$_8$) alkylene chain, optionally substituted with 1-6 hydroxy and/or —CO—NHR groups, and optionally interrupted by —O—, —S—, —N—, —N(R)—CO groups;

in case both groups B and X are absent, the two aromatic compounds are directly linked with a covalent bond with the proviso that the substituent R is H in at least one group of the compound.

Preferred compounds of general formula (I) are the compounds of general formula (III) in which:

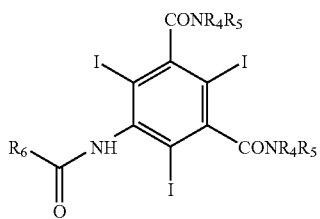

(III)

$R_4$, $R_5$, which can be the same or different, are H or a straight or branched ($C_1$-$C_3$)alkyl group, which can optionally be substituted with 1-2 hydroxy and/or alkoxy and/or hydroxyalkoxy groups;

$R_6$ is a straight or branched ($C_1$-$C_4$)alkyl group containing one or more hydroxy, alkoxy or acyloxy groups.

An example of particularly preferred compounds of general formula (I) and (III) are those compounds known under the names of Iopamidol and Iopromide (see scheme 1).

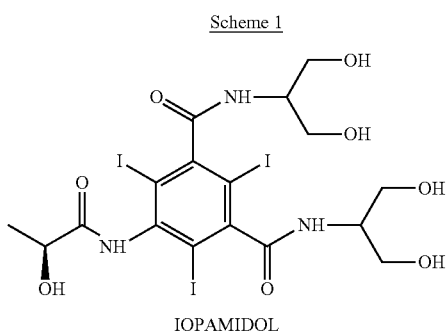

A further preferred group of iodinated contrast agents comprising amido functions comprises compounds of formula (IV):

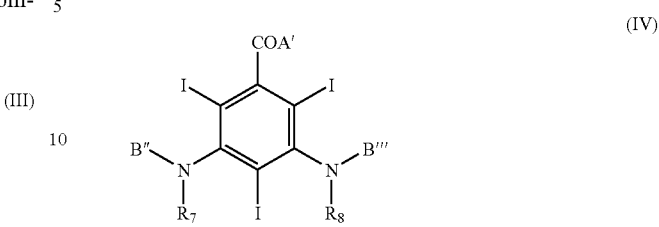

(IV)

in which:
A' is a OH or —$NHR_1$ group;
$R_1$ is a straight or branched ($C_1$-$C_6$)alkyl group, optionally substituted with 1-5 hydroxy and/or alkoxy and/or hydroxyalkoxy groups, or by a —NH—CO—$R_1$ or —CO—$NHR_1$ group, or $R_1$ is a carbohydrate residue;
B" and B'", which can be the same or different, are H or $R_1$, as defined above;
$R_7$ and $R_8$, which can be the same or different, are H, an acyl —$COR_1$ group, an alkyl group, a mono or polyhydroxyalkyl group or a carbohydrate residue;
with the proviso that at least one of the groups B", B'", $R_7$ or $R_8$ is H.

A particularly preferred example of the compounds of formula (IV) is Metrizamide (see scheme 2 and U.S. Pat. Nos. 3,701,771, 4,021,481), a water-soluble, soluble, non-ionic contrast agent having moderate toxicity and usually present as isomeric mixture.

A further preferred compound is diatrizoic acid (compound of formula IV), Renografin® (see scheme 2 and e.g. Radiology 140: 507-511, 1981; Biochimica et Biophysica Acta. 756, 106-110, 1983, Elsevier Biomedical Press and U.S. Pat. Nos. 4,192,859, 4,567,034 and 4,735,795) which is particularly suitable for the use according to the present invention.

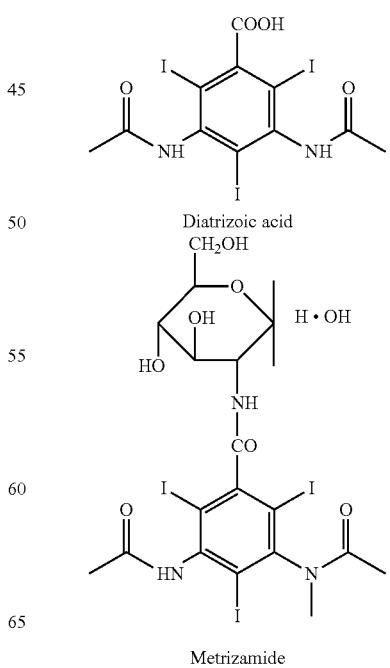

Examples of particularly preferred compounds of general formula (I) are the compounds reported in Scheme 3 below.

Scheme 3

| Non-proprietary name CAS [RN] | A | D | E |
|---|---|---|---|
| Metrizamide [31112-62-6] | —CONHCH(CHO)(CHOH)$_3$CH$_2$OH | —N(Me)Ac | —NH—Ac |
| Iopamidol [60166-93-0] | —CONHCH(CH$_2$OH)$_2$ | —CONHCH(CH$_2$OH)$_2$ | —NHCOCH(OH)CH$_3$ |
| Iopromide [73334-07-3] | —CONHCH(CH$_2$OH)$_2$ | —CON(Me)CH$_2$CH(OH)CH$_2$OH | —NHCOCH$_2$OMe |
| Iogulamide [75751-89-2] | —CONHCH$_2$CH(OH)CH$_2$OH | —CONHCH$_2$CH(OH)CH$_2$OH | —NHCOCO(CHOH)$_3$CH$_2$OH |
| Iodamide [440-58-4] | —COOH | —NHCOCH$_3$ | —CH$_2$NHCOCH$_3$ |
| Ioglucol [63941-73-1] | —CONHMe | —NHCO(CHOH)$_4$CH$_2$OH | —N(Ac)CH$_2$CH$_2$OH |
| Ioglucomide [63941-74-2] | —CONHMe | —NHCO(CHOH)$_4$CH$_2$OH | —NHCO(CHOH)$_4$CH$_2$OH |
| Ioglunide [56562-79-9] | —CONHCH$_2$CH$_2$OH | —NHCO(CHOH)$_4$CH$_2$OH | —N(Me)Ac |
| Iobitridol [136949-58-1] | —NHCOCH(CH$_2$OH)$_2$ | —CON(Me)CH$_2$CH(OH)CH$_2$OH | —CON(Me)CH$_2$CH(OH)CH$_2$OH |
| Iocibidol [79211-34-0] | —CON(Me)CH$_2$CH(OH)CH$_2$OH | —CONHCH$_2$CH(OH)CH$_2$OH | —CONH$_2$ |
| MP-10007 [77111-65-0] | —CONHCH$_2$CH$_2$OH | —NHCOCO(CHOH)$_3$CH$_2$OH | —NHCOCO(CHOH)$_3$CH$_2$OH |
| Iotriside [79211-34-0] | —CONH$_2$ | —CONHCH$_2$CH(OH)CH$_2$OH | —CON(Me)CH$_2$CH(OH)CH$_2$OH |
| Sodium diatrizoate [737-31-5] | —COONa | —NHCOCH$_3$ | —NHCOCH$_3$ |

Furthermore, particularly preferred are the compounds of formula (II) reported in the following Scheme 4.

Scheme 4

| Non-proprietary name CAS [RN] | A | D=E | B—X—B |
|---|---|---|---|
| Iofratol [141660-63-1] | —CONHCH(CH$_2$OH)$_2$ | —NHCOCH(OH)CH$_3$ | —CONHCH$_2$CH(OH)CH$_2$OH |
| Iotasul [71767-13-0] | —CON(Me)CH$_2$CH(OH)CH$_2$OH | —CON(Me)CH$_2$CH(OH)CH$_2$OH | —NHCOCH$_2$—S—CH$_2$CH$_2$CONH— |
| (WO 9208691) [143200-04-8] | —CONHCH$_2$CH(OH)CH$_2$OH | —NHCOCH$_2$OH | —CONHCH$_2$CH(OH)CH$_2$NHCO— |
| (WO 9208691) [143199-77-3] | —CONHCH(CH$_2$OH)$_2$ | —NHCOCH$_2$OH | —CONHCH$_2$CH(OH)CH$_2$NHCO— |
| (WO 9208691) [143200-00-4] | —CONHCH$_2$CH(OH)CH$_2$OH | —NHCOCH$_2$OH | —CONHCH$_2$C(CH$_2$OH)$_2$CH$_2$NHCO— |

Particularly preferred compounds for use according to the present invention comprise: Iopamidol, Iofratol, Iopromide, Metrizamide, Iogulamide, Ioglunide, Iobitridol, Iodamide, Sodium diatrizoate and other diatrizoic acid salts, and possible combinations thereof.

Other contrast agents for use according to the present invention are described in the following patents, herein incorporated by reference: U.S. Pat. Nos. 4,364,921, 4,284,620, 3,701,771, 4,001,323, 4,001,323, 4,250,113, 4,396,598, 4,192,859, 5,663,413, 4,239,747, 4,014,986, EP108 638, WO9208691, WO9515307, EP 33 426, U.S. Pat. Nos. 4,567, 034, 4,735,795, 5,869,024, 5,527,926, EP 431 838, EP 437 144.

The use of aqueous compositions of liposomes consisting of lipid molecules mono-, bi- or multi-layers as carriers for the compounds used as contrast agents is particularly preferred.

U.S. Pat. No. 4,192,859 discloses the preparation of liposomes made of lecithin and sterols, containing 20 to 60% by weight of contrast agent for use in imaging of organs, and in particular of endothelial reticule, cardiovascular system and also for lymphographies. Compounds that can be used for this purpose (U.S. Pat. No. 5,445,810) comprise, for example, the following contrast agents:

Iopamidol, metrizamide, diatrizoic acid, sodium diatrizoate, meglumine diatrizoate, acetrizoic acid and the soluble salts thereof, diprotizoic acid, Iodamide, Iodipamide sodium salt, Iodipamide meglumine salt, iodohippuric acid and the soluble salts thereof, iodometamic acid, iodopyracetiodo-2-pyridone-N-acetic acid, 3,5-diiodo-4-pyridone-N-acetic acid (Iodopiracet) and its diethyl ammonium salt, iothalamic acid, metrizoic acid and the salts thereof, ipanoic, iocetamic, iophenoxic acids and the soluble salts thereof, sodium tyropanoate, sodium hypodate and other similar iodinated compounds.

The preparation of liposomes containing opacifying contrast agents is disclosed in the following patents, herein incorporated by reference: U.S. Pat. No. 4,192,859, FR-A-2561101, U.S. Pat. No. 4,567,034, GB-A-134869, GB-A-2135268, GB-A-2135647, GB-A-2156345, GB-A-2157283, EP-A-179660, U.S. Pat. Nos. 4,192,859, 4,744,989, 4,830,858, 5,393,530, 5,702,722, 5,895,661, 5,980,937, 5,312,615, 5,445,810, 5,626,832.

Advantageous characteristics of the iodinated compounds described above are high water solubility, safety of use in vivo, pharmacological inertia, high chemical stability, low viscosity, low osmolarity and effective magnetization transfer in the presence of the radiofrequency signal applied at the absorption frequency of mobile protons.

Furthermore, said compounds have moderate in vivo toxicity and can be used at high dosages in diagnostic contrastographic applications.

Scheme 5 shows some data (Merck Index $12^{th}$ ed.) concerning toxicity of Iopamidol, Iopromide, Metrizamide and Sodium Diatrizoate.

Scheme 5
Iopamidol
4943. LD50 in mice, rats, rabbits, dogs (g/kg): 44.5; 28.2; 19.6; 34.7
Iopromide
4948. LD50 in mice, rats (g iodine/kg body weight): 16.5; 11.4 i.v.
Metrizamide
6077. LD50 i.v. in mice: 15 g/kg (Torsten); 18.6 g/kg (Salvenson); 11.5 g/kg (Sovak); 17.3 g/kg (Aspelin).
Sodium diatrizoate
2975. LD50 i.v. in rats: 14.7 g/kg (Langecker).

Moreover, the chemical stability of said compounds is considered an important feature which makes possible their treatment in autoclave at high temperatures, during sterilization of pharmaceutical injectable forms.

As an example, pharmacokinetic and pharmacotoxicy of Iopamidol, a molecule characterized by three amido protons that exchange with water protons, have been the object of a number of clinical studies (see e.g. Radiologica Diagnostica, 7, 73-82, 1982; Diagnostic Radiology, 7, 83-86, 1982; Drug Research, 40, 7, 1990; Clin. Pharmacokinet., 32, 180-193, 1997).

Interestingly, Iopamidol (see Experimental Section) used in MRI saturation transfer, allows to reduce even to 80% the signal from water at a 2.1 T magnetic field.

The compounds of the invention can be used in various radiographic and/or MRI procedures, including those concerning intravascular imaging such as myelography, urography, angiography (e.g. cerebral and peripheral angiography), cardiography (e.g. coronary arteriography and/or aortography), arthrography, for example of animal or human organs such as heart, breast, brain, knee, liver and central nervous system.

An interesting application of the MRI technique of the present invention is the use in angiographic diagnostics of blood vessels in organ perfusion imaging.

Also interesting is the possibility of using the magnetization transfer MRI technique, which allows differentiation between blood vessels and the more vascularized tissues of an organ and those characteristic of parenchyma.

An equation for rationalizing MRI magnetization transfer was first formulated by Forsen and Hoffman in J. Chem. Physics, 39 (11), 2892-2901 and is reported in the following:

$$Ms/Mo \approx [1/(1+KT)] \qquad (1)$$

wherein Ms is the value of the water proton signal during the saturation of the corresponding proton signal of the "exogen" molecule, Mo is the value of the signal without irradiation, i.e. in the presence of irradiation with the opposite frequency to that irradiated during the saturation phase, K is the exchange constant of mobile protons with water and T is the spin-lattice relaxation time of water protons (J.Magn. Res., 133, 36, 1998).

Magnetization transfer is affected by some parameters, such as intensity of the applied magnetic field, intensity of the radiofrequency field, chemical group involved in the prototropic exchange with water, pH, temperature of the medium, and water and "exogen" compound contents in the concerned tissue. An increase in the intensity of the radiofrequency field used for the saturation corresponds to an higher decrease of the bulk water signal. Both pH and temperature affect the proton exchange rate; in particular, an increase in temperature always induces an increase in the exchange rate, while pH catalyzes the exchange as it deviates from neutrality. Around pH 7, the exchange rate of the mobile protons is minimum and it increases when the solution is acidified (pH<7) or alkalinized (pH>7).

The value of the applied magnetic field is very important in that, for a given system, high $B_0$ values allows for higher exchange rates before incurring in a too large resonance broadening of exchangeable protons, which would make its efficient saturation with the irradiating field no longer possible.

The magnetization transfer technique can be carried out coupled with different kind of sequences, such as those known as "gradient or field echo" and "spin echo and fast spin echo". However, the sequences currently used in imaging are "gradient or field echo" rather than "fast spin echo".

The iodinated contrast agents are used at concentrations which vary depending on the compound used and the particular diagnostic use.

As a rule, the examination of a specific district of the human body determines the amount and the corresponding concentration used.

The pharmaceutical formulation of the contrast agent, which is usually an aqueous solution, contains for example 15 g of compound per 100 mL of solution, corresponding to a iodine amount ranging from 50 to 500 mg per mL. However, solutions containing lower amounts of the contrast agent can also be used.

The amount of solution used in the investigations carried out according to the invention is usually comparable to that used in radiological analysis and varies depending on the concerned body site: for example, 5 to 15 mL in myelography, 3 to 5 mL in radiculography and 1 to 2 mL in ventriculography. The solution or suspension containing the contrast agent can optionally be administered directly through the enteral route. For example, solutions or suspensions containing 1 to 100 mmoles of contrast agent, suspended in 1-2 l of physiologically compatible solution, can be used.

A further object of the present invention is an X ray and/or MRI procedure comprising the administration of a pharmaceutical composition containing a suitable amount of a compound or a mixture of compounds as defined above, in particular of general formula (I), (II), (III) and (IV), for the imaging and the recording of the image of an organ of the individual under observation.

The compounds of formula (I), (II), (III) and (IV) can be administered through the oral or enteral route.

For the parenteral administration, they are preferably formulated as sterile aqueous solutions or suspensions, with pH ranging from 6.0 to 8.5.

Said aqueous solutions or suspensions can be administered in concentrations ranging from 0.02 to 500 mM.

These formulations can be lyophilized and supplied as such, to be reconstituted just before the use. For the gastrointestinal use or for injection to body cavities, these agents can be formulated as a solution or suspension containing suitable additives in order to, for example, control viscosity, such as stabilizers, agents for controlling dissolution, anticoagulants, excipients used in the preparation of formulations and water soluble, physiologically compatible mineral salts.

The following examples illustrate the invention in greater detail.

EXAMPLE 1

Effect of pH on 50 mM Iopamidol Solutions

The exchange rate between amido protons and water is affected by the pH of the solution. When measurements are carried out at 2.1T magnetic field and at a temperature of 39° C., the transfer effect is maximum at pH 7.5. This effect decreases as pH becomes both more acid and more basic. When pH is below 6, or above 9, no effects are observed. In fact, outside this pH range from 6 to 9, the exchange is too fast for the purposes of the invention.

The effect on the decrease of the water signal in the corresponding magnetic resonance imaging, is anticipated by the measurements of R2 (=/1T2) of water protons as a function of the solution pH.

TABLE 1

R2 values (=1/T2) of water protons in a 50 mM Iopamidol solution as a function of pH at 2.1 and 9.34 T. Measurements were carried out with a JEOL EX-400 spectrometer at 25° C. using the CPMG sequence for the determination of T2.

| | PH | | | | | | | | | | |
|---|---|---|---|---|---|---|---|---|---|---|---|
| | 3.3 | 4.7 | 5 | 5.6 | 6.3 | 6.8 | 7.3 | 8.0 | 8.55 | 9.24 | 10.5 |
| R2 2.1T (s-1) | 0.46 | 0.60 | 0.62 | 0.64 | 1.10 | 1.64 | 1.93 | 1.12 | 0.54 | 0.39 | 0.30 |
| R2 9.34T (s-1) | 30.8 | 32.3 | 31.3 | 32.0 | 30.0 | 32.8 | 40.1 | 41.7 | 35.3 | 32.4 | 34 |

EXAMPLE 2

Effect of the Temperature on a 200 mM Iopamidol Solution

A 200 mM Iopamidol solution at pH=6.74 was investigated at 2.1T magnetic field intensity (JEOL EX-90 spectrometer). After irradiating the amido proton signal at 9.4 ppm, with attenuation of 300 dB, the area under the water signal was measured. Considering 100 the area of the water signal with irradiation at −9.4 ppm, a drastic reduction is observed following irradiation of the amido protons. The effect increases as temperature increase so that:

| | 15° C. | 25° C. | 39° C. |
|---|---|---|---|
| % residual signal | 39 | 30 | 24 |

EXAMPLE 3

Effect of Radiofrequency Field Intensity on a 200 Mm Iopamidol Solution.

A 200 Mm Iopamidol solution at pH=6.29 was investigated at 2.1T magnetic field intensity and at a temperature of 39° C. (JEOL EX-90 spectrometer).

Considering 100 the area of the water signal with irradiation at −9.4 ppm, its decrease (expressed as % residual signal) was evaluated in the presence of a rf field tuned at 9.4 ppm (signal of the amido protons).

A 40% residual signal value is measured when the irradiating field has an attenuation of 400 dB, which decreases to 15% when the attenuation is 300 dB.

EXAMPLE 4

Evaluation of the Contrast Ability of 50 mM Iopamidol

Imaging of a 50 mM Iopamidol aqueous solution recorded with an MRI Bruker Farmascan tomographer operating at 7.03 T. The sample is a plastic cylinder containing distilled water and a coaxial cone filled with the Iopamidol aqueous solution at pH 7.4.

Measurements were carried out at a temperature of about 21° C. using a spin echo sequence coupled with the saturation transfer technique.

The results are shown in FIG. 1.

The main parameters used in said sequence are listed in the following:
matrix 256×128
FOV 3.5 cm
slice thickness 2 mm
repetition time 4 s
echo time 18.3 ms
MTC power level 9 µT
n° of MTC pulses 380 with 104 µs pulse length (pulse shape=gauss).

The top left image was recorded applying the presaturation impulse at the amido protons resonance frequency (i.e. at 1280 Hz from water), the top right image was recorded applying the presaturation impulse at the frequency opposite to that of amido protons relative to bulk water (−1280 Hz), the bottom left image was obtained from the difference between the two first images, whereas the bottom right image was obtained without using the magnetization transfer technique.

EXAMPLE 5

Evaluation of the Contrast Ability of 25 mM Iopamidol

The procedures of Example 4 were followed, but using a 25 mM Iopamidol aqueous solution.

Figure 2:
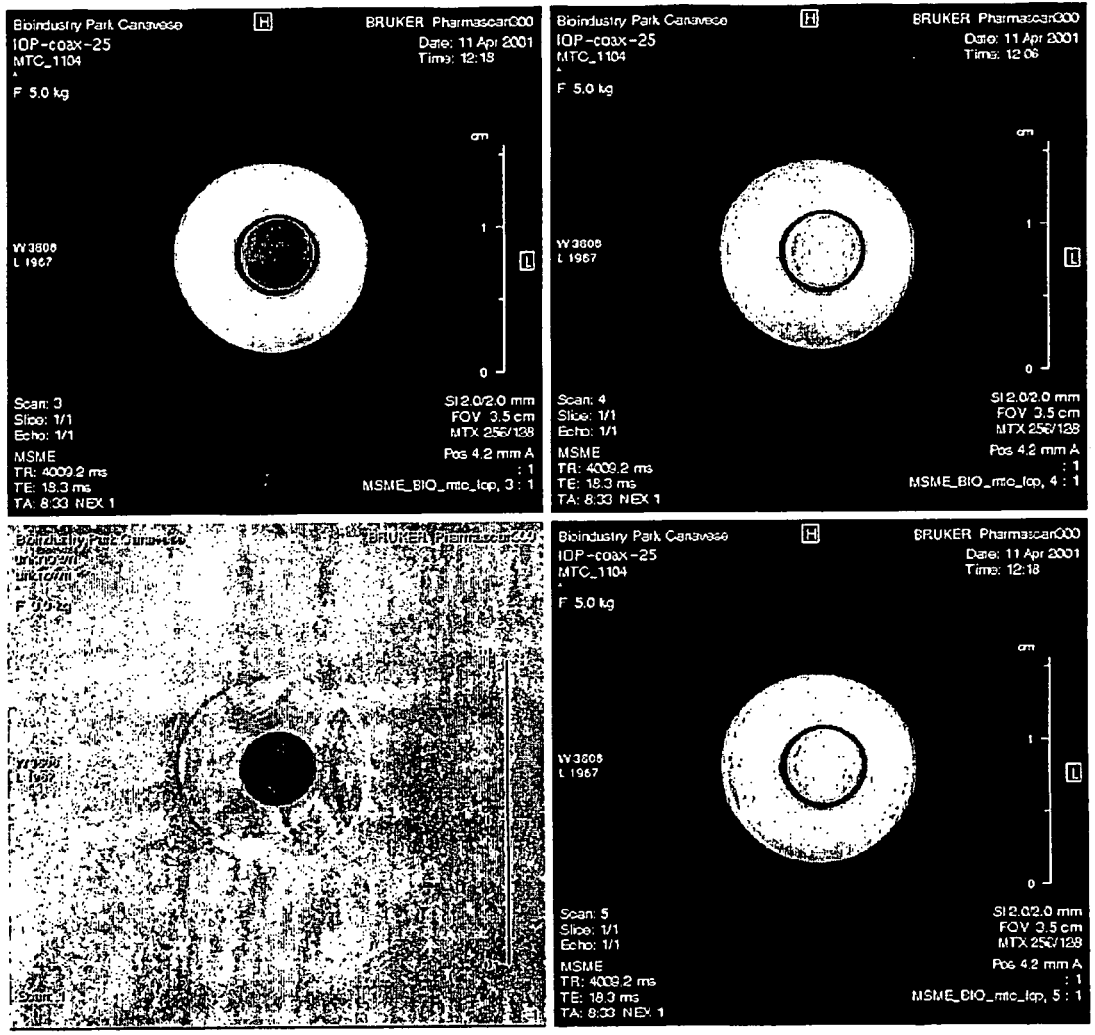

The results are shown in FIG. 2.

EXAMPLE 6

Evaluation of the Contrast Ability of 10 mM Iopamidol

The procedures of Example 4 were followed, but using a 10 mM Iopamidol aqueous solution.

Figure 3:
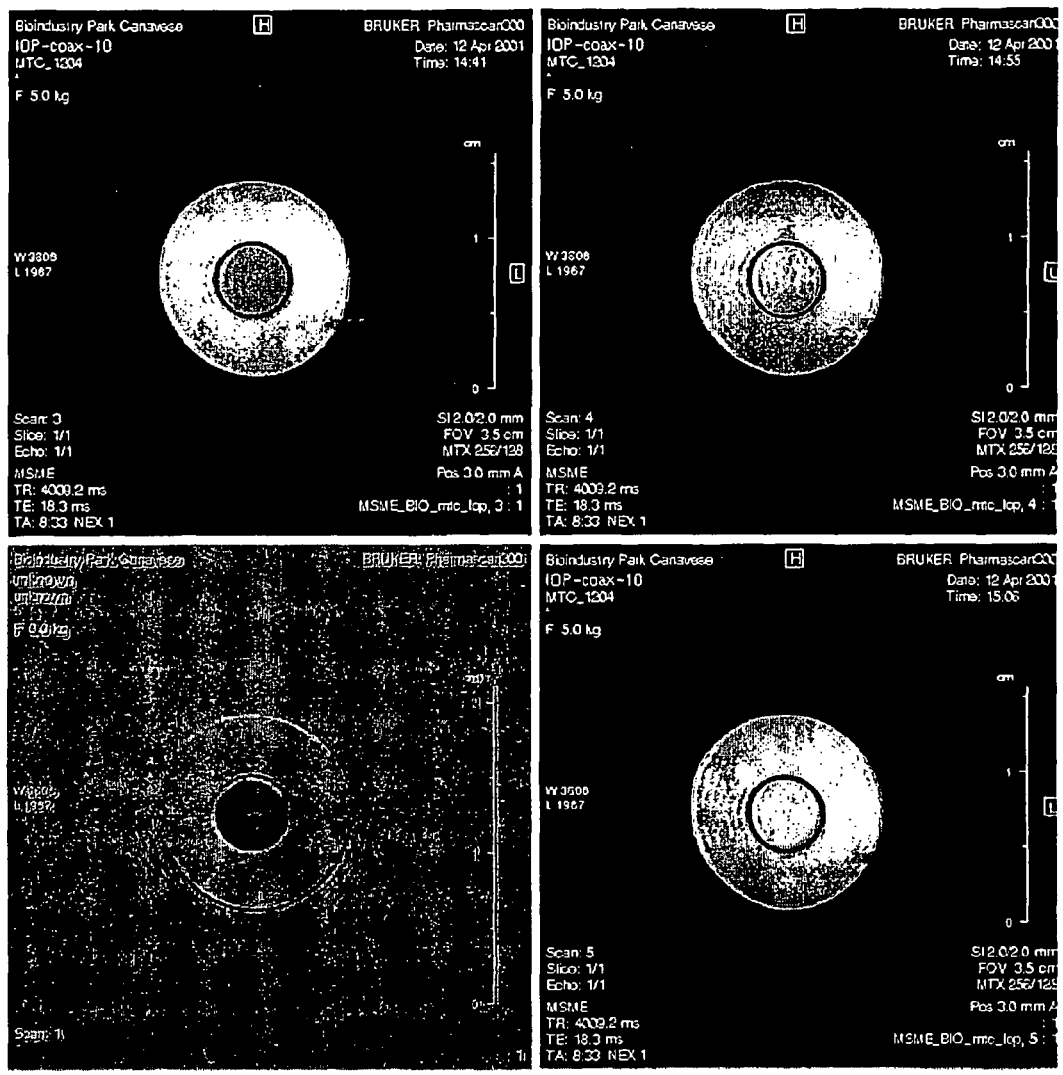

The results are shown in FIG. 3.

The invention claimed is:

1. A method of obtaining in vivo or in vitro images comprising the steps of:
   (a) administering a diagnostic formulation comprising one or more iodinated contrast agents comprising one or more mobile protons able to exchange with bulk water, to an individual or to an organ or other body part or tissue of the individual,
   (b) imaging, with magnetization transfer MRI techniques, by irradiating the mobile protons of the iodinated contrast agent with a radiofrequency field tuned on the resonance frequency of the concerned protons and inducing, through chemical exchange, saturation transfer to the bulk water signal, to obtain an image of an organ or other body part or tissue of the individual in which the saturation of the water signal causes a decrease in the water proton signal intensity, and
   (c) recording the image, wherein said iodinated contrast agents comprise at least one amido function and are iodinated aromatic compounds having a triiodinated aromatic ring bearing at the remaining positions straight or branched, functionally substituted organic residues or compounds comprising at least two triiodinated aromatic residues mutually covalently linked at one of the positions, either directly or through a straight or branched, functionally substituted organic residue, said aromatic ring being further substituted at the remaining positions by straight or branched, functionally substituted organic residues and in which the organic residues and the triiodinated aromatic ring are linked by amido functions.

2. The method of claim 1 wherein the imaging with magnetization transfer is coupled to "gradient or field echo" or "spin echo and fast spin echo" sequences.

3. The method of claim 1 wherein the iodinated contrast agents are compounds of formula (1):

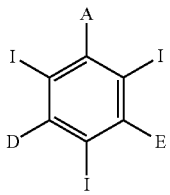

in which: A, D, E, which can be the same or different, are groups of formula —CON(R)R$_1$ —COOH, —CONH$_2$ or —N(R)—COR$_2$ or CH$_2$N(R)—COR$_2$; R is H or R$_1$, with the proviso that the substituent R is H in at least one group of the compound; RJ is a straight or branched (C$_1$-C$_6$) alkyl residue, optionally substituted with 1-5 hydroxy and/or alkoxy and/or hydroxy-alkoxy groups, or with a NH—CO—R$_1$ or —CO—N(R)R$_1$ group, or R$_1$ is a carbohydrate residue; R$_2$ is a straight or branched (C$_1$ -C$_6$) alkyl residue, optionally substituted with 1-5 hydroxy and/or alkoxy and/or hydroxyl-alkoxy groups and optionally interrupted by an oxo group.

4. The method of claim 3 wherein the imaging with magnetization transfer is coupled to "gradient or field echo" or "spin echo and fast spin echo" sequences.

5. The method of claim 1 wherein the iodinated contrast agents are compounds of formula (II):

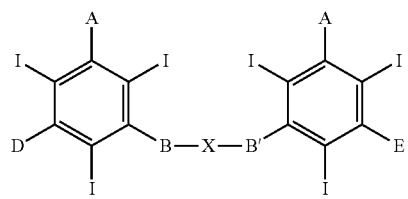

in which: A, D and E are as defined above; B and B', which can be the same or different, are selected from —CO—N(R)—, —N(R)—CO— or —N(COR$_3$)— groups, in which R is H or a residue of a straight or branched (C$_1$-C$_6$) alkyl group, optionally substituted with 1-5 hydroxy and/or alkoxy and/or hydroxyalkoxy groups; R$_3$ is a (C$_1$-C$_3$) alkyl residue, optionally substituted with 1-2 hydroxy or alkoxy or hydroxyalkoxy groups; X is a covalent bond or a straight or branched (C$_1$-C$_8$) alkylene chain, optionally substituted with 1-6 hydroxy and/or —CO—NHR groups, and optionally interrupted by —O—, —S—, —N—, —N(R)—CO groups; in case both groups B and X are absent, the two aromatic compounds are directly linked with a covalent bond with the proviso that the substituent R is H in at least one group of the compound.

6. The method of claim 5 wherein the imaging with magnetization transfer is coupled to "gradient or field echo" or "spin echo and fast spin echo" sequences.

7. The method of claim 1 wherein the iodinated contrast agents are compounds of formula (III):

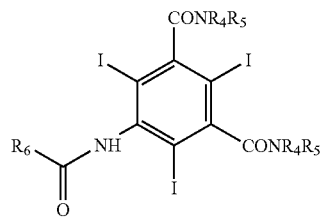

in which R$_4$, R$_5$, which can be the same or different, are H or a straight or branched (C$_1$-C$_3$) alkyl group, which can optionally be substituted with 1-2 hydroxy and/or alkoxy and/or hydroxyalkoxy groups; R$_6$ is a straight or branched (C-C$_4$) alkyl group containing one or more hydroxy, alkoxy or acyloxy groups.

8. The method of claim 7 wherein the imaging with magnetization transfer is coupled to "gradient or field echo" or "spin echo and fast spin echo" sequences.

9. The method of claim 1 wherein the iodinated contrast agents are compounds of formula (IV):

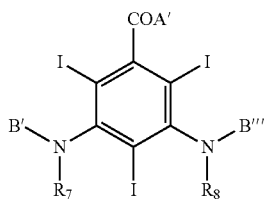

in which: A' is a OH or —NHR₁ group; R₁ is a straight or branched (C₁-C₆) alkyl group, optionally substituted with 1-5 hydroxy and/or alkoxy and/or hydroxyalkoxy groups, or by a —NH—CO—R₁ or —CO—NHR₁ group, or R₁ is a carbohydrate residue; B" and B'", which can be the same or different, are H or R₁, as defined above; R₇ and R₈, which can be the same or different, are H, an acyl —COR₁ group, an alkyl group, a mono or polyhydroxyalkyl group or a carbohydrate residue; with the proviso that at least one of the groups B", B'", R₇ or R₈ is H.

10. The method of claim 9 wherein the imaging with magnetization transfer is coupled to "gradient or field echo" or "spin echo and fast spin echo" sequences.

11. The method of claim 1 wherein the iodinated contrast agents are selected from Iopamidol, Iofratol, Ioprormide, Metrizamide, Iogulamide, Ioglunide, Iobitridol, Iodamide, Sodium diatrizoate and other diatrizoic acid salts, and combinations thereof.

12. The method of claim 1 wherein the MRI images are acquired before, during and after irradiation in the used radiofrequency field.

13. The method of claim 1 wherein the imaging is accomplished by magnetic resonance imaging in myelographic, urographic, cerebral or peripheral angiographic, cardiographic, coronary arteriographic or aortographic:, arthrographic intravascular imaging investigations.

14. The method of claim 12 wherein a radiographic investigation is carried out in vivo or in vitro before or after a magnetization transfer magnetic resonance investigation.

15. The method of claims 14 wherein the imaging is accomplished by radiographic: and MRI procedures including myelographic, urographic, cerebral or peripheral angiographic, cardiographic, coronary arteriographic or aortographic, arthrographic intravascular imaging investigations.

16. The method of claim 1 wherein the diagnostic composition consists of a liposome suspension of the iodinated contrast agents selected from the group consisting of iodinated aromatic compounds having a triiodinated aromatic ring bearing at the remaining positions straight or branched, functionally substituted organic residues or compounds comprising at least two triiodinated aromatic residues mutually covalently linked at one of the positions, either directly or through a straight or branched, functionally substituted organic residue, said aromatic ring being further substituted at the remaining positions by straight or branched, functionally substituted organic residues and in which the organic residues and the triiodinated aromatic ring are linked byamido functions, iodinated contrast agents of formula (I):

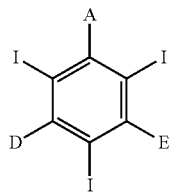

in which: A, D, E, which can be the same or different, are groups of formula —CON(R)R₁, —COOH, —CONH₂ or —N(R) —COR₂ or CH₂N(R) —COR₂; R is H or R₁, with the proviso that the substituent R is H in at least one group of the compound; R₁ is a straight or branched (C₁-C₆)alkyl residue, optionally substituted with 1-5 hydroxy and/or alkoxy and/or hydroxy-alkoxy groups, or with a NH—CO—R₁ or —CO—N(R)R₁ group, or R₁ is a carbohydrate residue; R₂ is a straight or branched (C₁-C₆)alkyl residue, optionally substituted with 1-5 hydroxy and/or alkoxy and/or hydroxyalkoxy groups and optionally interrupted by an oxo group, iodinated contrast agents of formula (II):

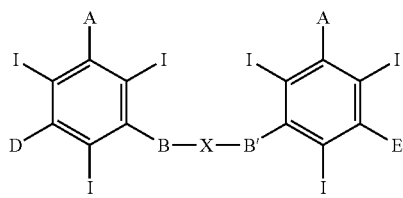

in which: A, D and E are as defined above; B and B', which can be the same or different, are selected from —CO— N(R) —, —N(R) —CO—or —N(COR₃) —groups, in which R is H or a residue of a straight or branched (C₁-C₆) alkyl group, optionally substituted with 1-5hydroxy and/or alkoxy and/or hydroxyalkoxy groups; R₃ is a (C₁-C₃)alkyl residue, optionally substituted with 1-2 hydroxy or alkoxy or hydroxyalkoxy groups; X is a covalent bond or a straight or branched (C₁-C₈)alkylene chain, optionally substituted with 1-6 hydroxy and/or —CO—NHR groups, and optionally interrupted by —0—, —S—, —N—, —N(R) —CO groups; in case both groups B and X are absent, the two aromatic compounds are directly linked with a covalent bond with the proviso that the substituent R is H in at least one group of the compound, iodinated contrast agents of formula (III):

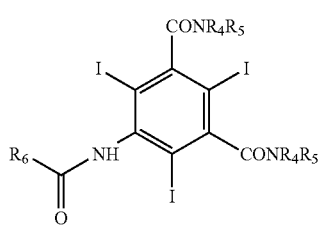

in which $R_4$, $R_5$, which can be the same or different, are H or a straight or branched ($C_1$-$C_3$) alkyl group, which can optionally be substituted with 1-2 hydroxy and/or alkoxy and/or hydroxyalkoxy groups; $R_6$ is a straight or branched ($C_1$-$C_4$)alkyl group containing one or more hydroxy, alkoxy or acyloxy groups, iodinated contrast agents of formula (IV):

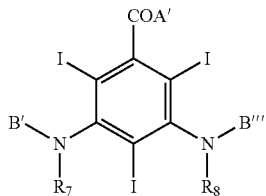

in which: A' is a OH or —$NHR_1$ group; $R_1$ is a straight or branched ($C_1$-$C_6$)alkyl group, optionally substituted with 1-5 hydroxy and/or alkoxy and/or hydroxyalkoxy groups, or by a —NH—CO—$R_1$ or —CO—$NHR_1$ group, or $R_1$ is a carbohydrate residue; B" and B'", which can be the same or different, are H or $R_1$, as defined above; $R_7$ and Rs, which can be the same or different, are H, an acyl —COR1 group, an alkyl group, a mono or polyhydroxyalkyl group or a carbohydrate residue; with the proviso that at least one of the groups B ", B '", $R_7$ or $R_8$ is H, Iopamidol, Iofratol, Ioprormide, Metrizamide, Iogulamide, Ioglunide, Iobitridol, Iodamide, Sodium diatrizoate, other diatrizoic acid salts and combination thereof together with suitable excipients.

17. The method of claim 1, wherein the iodinated contrast agent is capable of a saturation transfer to water which depends on the pH of the solution or the organ or other body part or tissue of the concerned individual.

18. The method of claim 1, wherein the iodinated contrast agent is capable of a saturation transfer to water which depends on the temperature of the solution or the organ or other body part or tissue of the concerned individual.

* * * * *